(12) United States Patent
Nees et al.

(10) Patent No.: US 10,436,740 B2
(45) Date of Patent: Oct. 8, 2019

(54) SENSOR ELEMENT FOR DETECTING AT LEAST ONE PROPERTY OF A MEASURING GAS IN A MEASURING GAS SPACE, CONTAINING A GROUND, IMPREGNATED SLIP LAYER

(71) Applicant: Robert Bosch GmbH, Stuttgart (DE)

(72) Inventors: Siegfried Nees, Talheim (DE); Petra Kuschel, Leonberg-Hoefingen (DE); Harry Braun, Heimsheim (DE); Jens Schneider, Leonberg (DE)

(73) Assignee: Robert Bosch GmbH, Stuttgart (DE)

( * ) Notice: Subject to any disclaimer, the term of this patent is extended or adjusted under 35 U.S.C. 154(b) by 196 days.

(21) Appl. No.: 15/499,286

(22) Filed: Apr. 27, 2017

(65) Prior Publication Data

US 2017/0248540 A1 Aug. 31, 2017

Related U.S. Application Data

(62) Division of application No. 14/409,976, filed as application No. PCT/EP2013/059764 on May 13, 2013, now abandoned.

(30) Foreign Application Priority Data

Jun. 25, 2012 (DE) ........................ 10 2012 210 725

(51) Int. Cl.
*G01N 27/407* (2006.01)
*H01M 4/88* (2006.01)
*G01N 27/409* (2006.01)

(52) U.S. Cl.
CPC ....... *G01N 27/4071* (2013.01); *G01N 27/409* (2013.01); *G01N 27/4072* (2013.01);
(Continued)

(58) Field of Classification Search
CPC .............. G01N 27/4071–4077; G01N 27/409
See application file for complete search history.

(56) References Cited

U.S. PATENT DOCUMENTS

| 5,106,654 A | 4/1992 | Isenberg |
| 5,139,829 A * | 8/1992 | Minoha .............. G01N 27/4075 427/123 |

(Continued)

FOREIGN PATENT DOCUMENTS

| DE | 413503 A1 | 4/1993 |
| DE | 102008054617 A1 | 6/2010 |

(Continued)

OTHER PUBLICATIONS

International Search Report dated Aug. 7, 2013, of the corresponding International Application PCT/EP2013/059764 filed May 13, 2013.

(Continued)

*Primary Examiner* — Maris R Kessel
(74) *Attorney, Agent, or Firm* — Norton Rose Fulbright US LLP; Gerard Messina

(57) ABSTRACT

A method for manufacturing a sensor element for detecting (i) a gas component in a measuring gas or (ii) a temperature of the measuring gas includes: introducing at least one functional element into at least one slip at least once in such a way that a slip layer is applied to the functional element, the functional element including at least one solid electrolyte and at least one functional layer; sintering the slip layer on the functional element; grinding the slip layer at least in the area of the at least one functional layer; impregnating the slip layer; and thermally treating the impregnated slip layer.

8 Claims, 1 Drawing Sheet

(52) U.S. Cl.
CPC ...... *G01N 27/4075* (2013.01); *H01M 4/8885* (2013.01); *H01M 4/8889* (2013.01); *H01M 4/8892* (2013.01); *G01N 27/4077* (2013.01)

(56) References Cited

U.S. PATENT DOCUMENTS

| | | |
|---|---|---|
| 5,423,973 A | 6/1995 | Friese |
| 2004/0154920 A1* | 8/2004 | Schneider .......... G01N 27/4075 204/431 |
| 2004/0158971 A1* | 8/2004 | Kawashima ....... G01N 27/4071 29/592.1 |
| 2005/0274615 A1 | 12/2005 | Naito et al. |
| 2010/0163411 A1 | 7/2010 | Su et al. |

FOREIGN PATENT DOCUMENTS

| | | |
|---|---|---|
| EP | 0239771 A2 | 10/1987 |
| EP | 0467692 A2 | 1/1992 |
| EP | 0686847 A2 | 12/1995 |
| JP | 2005-195516 | 7/2005 |
| JP | 2007-218893 A | 8/2007 |
| JP | 2012-93330 A | 5/2012 |

OTHER PUBLICATIONS

Konrad Reif: Sensoren im Kraftfahrzeug [Sensors in the motor vehicle], 1st edition, 2010, pp. 160-165.

\* cited by examiner

SENSOR ELEMENT FOR DETECTING AT LEAST ONE PROPERTY OF A MEASURING GAS IN A MEASURING GAS SPACE, CONTAINING A GROUND, IMPREGNATED SLIP LAYER

CROSS REFERENCE TO RELATED APPLICATIONS

This application is a divisional application of, and claims the benefit under 35 U.S.C. § 120 of, U.S. patent application Ser. No. 14/409,976, filed Dec. 19, 2014, which is a national phase to International Application No. PCT/EP2013/059764, filed May 13, 2013, and claims priority to German Patent Application No. 10 2012 210 725.8, filed Jun. 25, 2012 all of which are hereby incorporated by reference in their entireties.

BACKGROUND OF THE INVENTION

1. Field of the Invention

The present invention relates to a sensor element and a method for detecting a measuring gas.

2. Description of the Related Art

A large number of sensor elements and methods for detecting at least one property of a measuring gas in a measuring gas space are known from the related art. In principle, this may involve arbitrary physical and/or chemical properties of the measuring gas, whereby one or multiple properties may be detected. The present invention is described below, in particular, with reference to a qualitative and/or quantitative detection of a gas component of the measuring gas, in particular, with reference to a detection of an oxygen content in the measuring gas. The oxygen content may, for example, be detected in the form of a partial pressure and/or in the form of a percentage. Alternatively or in addition, other properties of the measuring gas are also detectable, however.

For example, such sensor elements may be designed as so-called lambda sensors, as are known for example, from Konrad Reif (publisher): Sensoren im Kraftfahrzeug [Sensors in the motor vehicle], $1^{st}$ edition, 2010, pp 160-165. With broadband lambda sensors, in particular with planar broadband lambda sensors, it is possible, for example, to determine the oxygen concentration in the exhaust gas in a large area, and thereby deduce the air-fuel ratio in the combustion chamber. The air ratio λ describes this air-fuel ratio.

Ceramic sensor elements, in particular, are known from the related art, which are based on the use of electrolytic properties of certain solid bodies, i.e., on ion-conductive properties of these solid bodies. These solid bodies may be, in particular, ceramic solid electrolytes such as, for example, zirconium dioxide ($ZrO_2$), in particular, yttrium-stabilized zirconium dioxide (YSZ) and/or scandium-doped zirconium dioxide (ScSZ), which may contain small additional amounts of aluminum oxide ($Al_2O_3$) and/or silicon oxide ($SiO_2$).

Such sensors are subject to increasing functional demands. In particular, a rapid operational readiness of lambda sensors after an engine start plays a significant role. This readiness is influenced essentially by two aspects. The first aspect relates to a rapid heating of the lambda sensor to its operating temperature above 600° C., which may be achieved by a corresponding design of a heating element or by a reduction of the area to be heated. The second aspect relates to the robustness against thermal shock as a result of water hammer during an operation. The aforementioned thermal shock is due to the fact that for a certain period of time after the engine start, the temperature in the exhaust pipe lies below the dew point for water, so that water vapor formed during fuel combustion is able to condense in the exhaust pipe. This leads to the formation of water droplets in the exhaust pipe. Due to the impact of water droplets, the heated ceramic of the lambda sensor may be damaged or even destroyed as a result of thermal stresses or fractures in the sensor ceramic. For this reason, lambda sensors have been developed which have a porous ceramic protective layer on their surface, also referred to as a thermal shock protection layer. This protective layer ensures that water droplets impacting the lambda sensor are distributed over a wide area, thereby reducing the locally occurring temperature gradients in the solid body electrolyte or sensor ceramic. Thus, in the heated state, these lambda sensors tolerate a certain droplet size of condensed water without being damaged. The protective layer is normally applied to the sensor element in an additional method step. Various materials such as, for example, aluminum oxide or spinel ($MgAl_2O_4$) and coating techniques such as, for example, spray processes or immersion processes are used for this purpose.

In spite of the numerous advantages of the methods for manufacturing sensor elements for lambda sensors known from the related art, there is nevertheless potential for improvement.

BRIEF SUMMARY OF THE INVENTION

Therefore, a method for manufacturing a sensor element for detecting at least one property of a measuring gas in a measuring gas space, and a sensor element manufacturable according to this method are provided, which at least largely avoid the disadvantages of known methods and sensor elements, and in which the robustness against thermal shock may be improved using a cost-effective method.

The method according to the present invention includes the following steps, preferably in the sequence cited, whereby in principle another sequence is also conceivable, however:

introducing, in particular, immersing at least one functional element at least once into at least one slip in such a way that a slip layer is applied to the functional element, the functional element including at least one solid electrolyte and at least one functional layer, sintering the slip layer on the functional element, grinding the slip layer at least in the area of the at least one functional layer, impregnating the slip layer, and thermally treating the impregnated slip layer.

Moreover, the method may include one or multiple additional steps which are not mentioned. In addition, individual or multiple or all method steps may be carried out simultaneously, chronologically overlapping or repeatedly.

The functional element may be introduced, for example, by immersion into the slip. Immersion into the slip may occur, in particular, completely or also only partially. The functional element may be introduced repeatedly into the slip. At least one drying process may be carried out between the repeated introductions of the functional element into the slip. Impregnation may be carried out with the aid of a precious-metal-containing and/or getter-containing solution. For example, the impregnation may contain platinum, palladium, rhodium and/or include a getter-containing preparation such as, for example, LiOH, $MgCl_2$. Prior to introduction into the slip, a cavity forming layer may be applied to the functional element. After sintering and grinding, the at least one slip layer may have a thickness of 50 µm to 600 µm, preferably of 150 µm to 350 µm, and even more preferably 200 µm to 300 µm, for example, 250 µm. The slip layer may be sintered together with a functional layer present in the unsintered state. It is equally conceivable, however, for the slip layer to be applied to a previously sintered functional element and to be subsequently burned in. The slip may be, in particular, a highly fluid immersion slip capable of forming drops, i.e., a slip based on organic solvents or which is water-based. In particular, the slip may be capable of forming drops and be filled with oxidic solids such as, for example, aluminum oxide, zirconium oxide and/or titanium oxide, pore forming agents such as, for example, vitreous carbon or wax, fine-particle precious metal powders or fine-particle salts such as, for example, metallic platinum powder, palladium powder, rhodium powder or, for example, chlorides or nitrates thereof, fractions of binders and organic additives such as, for example, wetting agents, dispersants, defoamers for adjusting the rheological properties, solvents or water. Such slips are described, for example in published German patent application document DE 28 52 647 A1 and European patent document EP 0 386 027 B1, and their formulas, compositions and methods of preparation are incorporated by reference herein. For example, the slip may be composed as follows: 40.0% by weight of butylcarbitol as a solvent, 1.5% by weight of polyvinylbutyral as a binder, 2.0% by weight of polyethylene (PE) wax as a pore forming agent, 0.5% by weight of a wetting agent, 42.0% by weight of yttrium-stabilized zirconium dioxide (YSZ), and 14.0% by weight of aluminum oxide.

The immersion coating with the slip may take place, for example, by simple or repeated immersion with intermittent drying, different slip formulas being advantageously used during repeated coating, for example. The slip layers may, for example, include a porosity increasing from an inner to an outer layer. Each application of a slip layer may be followed by a drying process, such as for a period of less than one hour at temperatures of less than 250° C. Following the application of all slip layers, a subsequent sintering may be carried out at a temperature of 1200° C. to 1450° C.

Grinding may take place, for example, using a corundum grinding belt or a grinding disk. This offers the advantage of grinding multiple times. For example, grinding may take place above an outer electrode or measuring electrode of a lambda sensor or over a gas entry hole of a broadband lambda sensor. The areas of the slip layer having a greater thickness may, for example, delimit or define an underlying cavity. Grinding may take place at least in the area of the at least one functional layer, i.e., in an area which overlaps the functional layer in a direction of a layer structure of the sensor element.

Impregnation may take place, for example, using a platinum-containing and/or rhodium-containing impregnation solution. For example, a drip process may be used for applying the precious metal-containing solution to the grinding site, in which a targeted, local wetting occurs only above the electrode due to a savings of precious metal. Impregnation may also take place, for example, using a getter-containing solution. An immersion method is also conceivable, however, in which the ground slip layer is immersed into the impregnating fluid. In this case, the surface produced by grinding has a higher absorption capacity for the impregnating fluid than the adjacent unground areas. The effect of this is a lower porosity and absorption capacity for the impregnating fluid on the unground surface and a high absorption capacity for the impregnating fluid caused, for example, by a higher open porosity at the ground site. Finally, the impregnated slip layer undergoes a thermal treatment such as, for example, a single baking of the impregnation, and a functional test on the sensor element.

As a particular variant of the method according to the present invention, a cavity forming layer may be applied prior to a slip coating, for example, on the electrode side above a gas entry hole, provided, for example, with the aid of screen printing. The cavity forming layer may, for example, be a highly filled vitreous carbon paste which leaves behind a cavity after sintering. Thereafter, the slip may then be dip coated, followed by a grinding process.

A sensor element according to the present invention includes a functional element, which includes at least one solid electrolyte and at least one functional layer, and at least one impregnated slip layer on the functional element, the slip layer being ground at least in the area of the at least one functional layer. The at least one slip layer may have a thickness of 50 µm to 600 µm, preferably from 150 to 350 µm, and even more preferably of 200 µm to 300 µm, for example 250 µm. The slip layer may have an open porosity of 10% to 60%, preferably of 15% to 50% and even more preferably of 15% to 30%. The slip layer may have a porosity gradient, the porosity gradient increasing from the side of the slip layer facing the functional element in the direction of the side of the slip layer facing away from the functional element. A cavity may be situated between the slip layers in the functional element. The functional element may include a layer structure having at least one first electrode, having at least one second electrode and having the solid electrolyte, the solid electrolyte connecting the first electrode and the second electrode, the second electrode being formed separately from the measuring gas space by at least one layer of the layer structure, the second electrode being connected to the measuring gas space via at least one gas entry path, the gas entry path including at least one gas entry hole in the layer structure, the cavity being situated between the gas entry hole and the slip layer.

The layer structure may, for example, be formed in such a way that the first electrode and the second electrode are situated on opposite sides of the solid electrolyte, for example, on opposite sides of a solid electrolyte layer such as, for example, a solid electrolyte foil or a solid electrolyte paste. Alternatively or in addition, however, the at least two electrodes may also be situated on the same sides of the solid electrolyte. The electrodes and the solid electrolyte form together preferably at least one cell. The sensor element may be designed as a single cell sensor element with just one individual cell, which may be used, for example, as a Nernst cell or also as a pump cell. Alternatively, the sensor element may also be designed as a multi-cellular sensor element having several of such cells, which may also implement different functions. For example, at least one pump cell and at least one Nernst cell may be provided.

At least one of the at least two electrodes, hereinafter also referred to as the second electrode is situated in the interior of the layer structure without weighting or sequencing these electrodes. In other words, the second electrode is formed separately from the measuring gas space by at least one layer of the layer structure. In particular, this at least one layer may be at least one solid electrolyte layer. The at least one second electrode is thus situated in a deeper layer level of the layer structure, i.e., in a layer level which is formed remotely from a surface of the solid electrolyte facing the measuring gas space. The at least one additional electrode, i.e., the at least one first electrode according to the nomenclature used herein, may also be situated in a deeper layer level; it may, however, also be situated above, i.e., for example, on a surface of the layer structure facing the measuring gas space. For example, the first electrode may be designed as an outer electrode and may be separated from the measuring gas space, for example, solely by a gas-permeable porous protective layer, and otherwise, for example, is in direct gas exchange with the measuring gas space. Various embodiments are possible.

The at least one second electrode in this case is connected to the measuring gas space via at least one gas entry path. A gas entry path is understood in general to mean an element via which an exchange may take place between the measuring gas space and the second electrode, whereby a complete gas exchange or also merely an exchange of individual gas components may be ensured. For example, the gas entry path may include one or multiple holes, channels, openings or the like. In particular, the gas entry path may be designed in such a way that it ensures a subsequent flow and/or subsequent diffusion of gas to the second electrode from the measuring gas space or in the opposite direction, for example, a subsequent flow and/or a subsequent diffusion of oxygen. The gas entry path includes at least one gas entry hole in the layer structure.

A gas entry hole in this case is understood to mean an opening which extends through the layer structure, in particular, the solid electrolyte along an axis, in particular, through the at least one layer which separates the at least one second electrode from the measuring gas space. The gas entry hole may, in principle, have an arbitrary cross section, for example, a round cross section or a polygonal cross section. The gas entry hole may, in particular, run perpendicularly to the layer levels of the layer structure, and may, for example, have a cylindrical shape, at least in sections, for example, a plain cylindrical shape.

The at least one second electrode may be situated, in particular, in an electrode cavity. This electrode cavity may be situated in an interior of the layer structure and may be formed, for example, as an open cavity. Alternatively, this electrode cavity may also be completely or partially filled with a gas-permeable, porous material, for example, with a gas-permeable aluminum dioxide. The electrode cavity may, in particular, be connected to the gas entry hole via at least one diffusion barrier. In this case, therefore, the gas entry path to the at least one second electrode includes the gas entry hole, the diffusion barrier or a channel in which the diffusion barrier is situated, as well as the electrode cavity.

A diffusion barrier is understood within the scope of the present invention in general to mean an element which prevents, or at least slows a direct subsequent flow of gas out of the gas entry hole into the electrode cavity. Thus, a diffusion barrier is an element which provides a high flow resistance, whereas a diffusion of gas or gas components through the diffusion barrier is comparatively easy. The diffusion barrier may, for example, include a porous ceramic element, in particular, a fine-pored aluminum oxide. If such a diffusion barrier is provided, it is in particular preferable if the diffusion barrier is designed recessed in relation to the gas entry hole. A recessed diffusion barrier in this case is understood to mean a diffusion barrier which is not directly adjacent to the gas entry hole, but rather is recessed in relation to the hole. For example, the diffusion barrier may be situated in a channel or in some other opening which is a part of the gas entry path, whereby, however, the diffusion barrier does not reach the transition between this channel or this opening and the gas entry hole directly, but rather ends at a distance from this transition. The advantage of this recessed or retracted diffusion barrier is that during manufacture of the gas entry hole, this barrier is not damaged, as a result of which contamination of the diffusion barrier could occur or as a result of which irregularities could occur when setting the limit current, which is determined by the width of the diffusion barrier. In addition, the aforementioned design improves stability during continuous operation, in particular with respect to a sooting, for example, by particles made of ash such as, for example, oil ash and/or metal oxides.

In the manufacturing method for a sensor element, the layer structure may be manufactured by using sheeting techniques and/or thick film techniques and/or other ceramic layering techniques.

As mentioned previously, an introduction, in particular, an immersion, may occur completely or only partially. The functional element may be a ceramic solid electrolyte present in a sintered state. However, it is equally conceivable for the electrolyte to be present in the unsintered state or in the annealed or pre-sintered state. Sintering may occur in such a way that the functional element is present in the unsintered state and is sintered together with the applied slip layer.

A slip is understood within the scope of the present invention to mean a fluid, pulpy to viscous water mineral or solvent-mineral mixture, which may also be referred to as a compound, for manufacturing ceramic products.

A functional element is understood within the scope of the present invention to mean an element which includes at least one solid electrolyte and at least one functional layer. A solid electrolyte is understood within the scope of the present invention to mean a component which is based on the use of the electrolytic properties of certain solids, that is, on the ion-conductive properties of these solids. These solids may include, in particular, ceramic solid electrolytes such as, for example, zirconium dioxide ($ZrO_2$), in particular yttrium-stabilized zirconium dioxide (YSZ) and/or scandium-doped zirconium dioxide (ScSZ), which may contain small additional amounts of aluminum oxide ($Al_2O_3$) and/or silicon oxide ($SiO_2$). A functional layer is understood within the scope of the present invention to mean an element which is selected from the group composed of: electrode, conductor path, diffusion barrier, diffusion gap, reference gas channel, heating element, Nernst cell and oxygen pump cell. In particular, it is understood to mean those elements which fulfill the essential chemical and/or physical and/or electrical and/or electrochemical functions of a lambda sensor. The functional element may be present in the unsintered or pre-sintered state. Correspondingly, the functional element may be a finished functional element or a preliminary stage thereof, which must still be sintered.

An impregnating fluid or impregnating solution is understood within the scope of the present invention to mean a fluid or solution which facilitates the adjustment of the normal position in the slip layer, as well as the function as a protective layer against erosive or corrosive effects from the exhaust gas. The impregnating fluid may be based on precious metals. The precious metals, in particular from the platinum group, catalyze the adjustment of the thermodynamic balance and thereby set the sensor element normal position near the stoichiometric point, i.e., at $\lambda=1$. Also conceivable, however, are non-precious metal-based getter-containing solutions, i.e., materials as getters for harmful substances such as, for example, lead, silicon, phosphorus, zinc, which could adversely affect the electrode function, and which take effect from the exhaust gas. Also possible is the use of mixed oxides based on at least one alkaline oxide or alkaline earth metal oxide on the one hand and a thermally stable oxide of an element having the valence of at least three, preferably based on groups IIIa, IIIb or IVb of the periodic table of elements. Thus, non-precious metal-based getters such as, for example, LiOH, $MgCl_2$, are also possible as impregnating fluid.

A pore forming agent is understood within the scope of the present invention to mean any material which is constituted to render a layer or component containing this material porous or lighter. For example, the pore forming agent may be contained in a slip in order to give it a certain porosity. Examples of pore forming agents are vitreous carbon, sawdust and cork dust, starch, carbon dust, polymer beads or polymer fibers, in particular, short fibers. In particular, it is understood to mean carbon-based materials which combust during so-called sintering and leave behind cavities in the process.

Porosity is understood within the scope of the present invention to mean the ratio of the cavity volume to the total volume of a substance or mixture of substances as a dimensionless measured variable. This measured variable may be indicated, in particular, in percentages. In this case, the open porosity is understood to mean the portion of the cavity volume of those cavities as part of the total volume which is in contact with one another and with the ambient air.

A cavity forming layer is understood within the scope of the present invention to mean a layer made of at least one material, which may be preferably cleanly removed by chemical processes such as, for example, hydrolysis, solvent extraction, and/or thermal processes such as, for example, burn-off, debinding, sintering. This material may, for example, contain a pore forming agent, which combusts during sintering. These are starch, carbon dust, or polymer beads, for example. In particular, this is understood to mean carbon-based materials, which combust during so-called sintering and leave behind cavities in the process. Carbon dust in the form of lamp black, for example, may be used as a cavity forming agent for manufacturing planar lambda sensors. Purely organic components and/or a carbon modification may also be used such as, for example, graphite, vitreous carbon and carbon black.

The method according to the present invention for manufacturing a sensor element is easily adaptable to various functional element lengths. In particular, a thick and dense protective layer of a planar sensor element may be obtained on all sides, i.e., a so-called all-round protection, in particular, of all edges in the hot area of the sensor element. Moreover, a precise porosity setting is possible by adjusting the slip composition, the slip preparation conditions, the layer thickness and/or the sintering conditions. A single coating or repeated coating is also possible. On the whole the method according to the present invention is cost-effective.

DETAILED DESCRIPTION OF THE INVENTION

Figure 1:
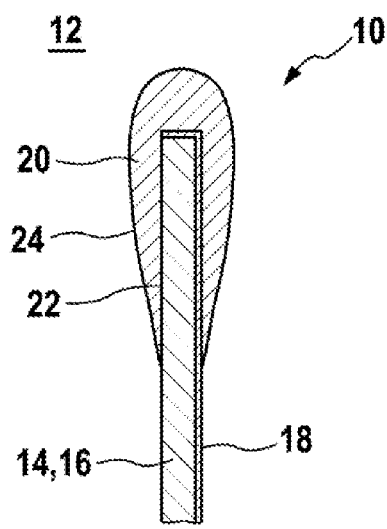
FIG. 1 shows a view of a cross section perpendicular to a direction of a layer structure of a sensor element according to the present invention to which a slip layer is applied.

FIG. 1 shows a view of a cross section perpendicular to a direction of a layer structure of a sensor element 10 according to the present invention. Sensor element 10 depicted in FIG. 1 may be used to verify physical and/or chemical properties of a measuring gas, whereby one or multiple properties may be detected. The present invention is described below, in particular, with reference to a qualitative and/or quantitative detection of a gas component of the measuring gas, in particular with reference to a detection of an oxygen content in the measuring gas. The oxygen content may be detected, for example, in the form of a partial pressure and/or in the form of a percentage. However, other types of gas components are, in principle, also detectable, for example, nitrogen oxides, hydrocarbons and/or hydrogen. Alternatively or in addition, other properties of the measuring gas are also detectable, however. The present invention may be used, in particular, in the field of automotive engineering, so that measuring gas space 12 may, in particular, be an exhaust system of an internal combustion engine, and the measuring gas may, in particular, be an exhaust gas.

Sensor element 10, as an exemplary component of a planar lambda sensor, includes a functional element 14 having a solid electrolyte 16 in the form of a ceramic solid electrolyte layer 16 and having a functional layer 18. Functional layer 18, for example, is an outer electrode or measuring electrode of a lambda sensor. In general, functional element 14 may have a layer structure, in which, for example, solid electrolyte 16 is constructed of multiple electrolyte films. One or multiple functional layers 18 may be situated, for example, between and on these electrolyte films such as, for example, a heating element and multiple electrodes.

Sensor element 10 also includes an impregnated slip layer 20. Slip layer 20 may be situated, for example, in the form of a drop on solid electrolyte 16. Slip layer 20 may cover the entire surface or a portion of the surface of solid electrolyte 16. Slip layer 20 is ground, at least in the area of the at least one functional layer 18. Slip layer 20 may, for example, have a thickness of 50 μm to 600 μm, preferably of 150 μm to 350 μm, and even more preferably of 200 μm to 300 μm, for example, 250 μm. Slip layer 20 contains, in particular, oxidic solids, in particular, aluminum oxide, zirconium oxide and/or titanium oxide. Slip layer 20 also contains finely dispersed precious metals such as, for example, platinum, palladium, rhodium. Slip layer 20 may have an open porosity of 10% to 60%, preferably of 15% to 50%, and even more preferably of 15% to 30%, for example, 20%. For example, slip layer 20 may have a porosity gradient. The porosity in this case may increase from a side 22 of slip layer 20 facing functional element 14 in the direction of a side 24 of slip layer 20 facing away from functional element 14.

In particular, slip layer 20 is impregnated. The impregnation may be introduced, for example, by a precious metal-containing and/or getter-containing preparation during manufacture of sensor element 10, as is described in greater detail below. Slip layer 20 acts as a thermal shock protection layer, the impregnation ensuring that functional element 14 is not choked by harmful substances of the measuring gas, because the harmful substances from the exhaust gas such as, for example, silicon, adhere to or adsorb on the impregnation and therefore do not reach functional layer 18. Moreover, the precious metals act as a catalyst in order to decompose non-combusted components of the measuring gas. The aforementioned porosity ensures that per time unit only a specific amount of measuring gas passes out of measuring gas space 12 to functional layer 18.

Sensor element 10 may be manufactured, in particular, as described below.

Figure 2:
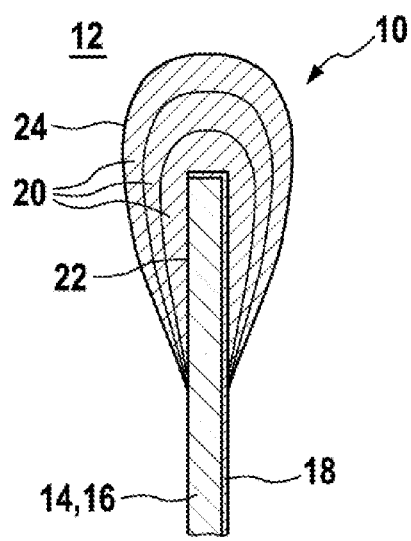
FIG. 2 shows a view of a cross section perpendicular to a direction of a layer structure of a sensor element according to the present invention to which three slip layers are applied.

A functional element 14, which includes at least one solid electrolyte 16 and at least one functional layer 18, is initially introduced into a slip. For example, functional element 14 may be immersed just once into the slip. In this way, a slip layer 20 is applied to functional element 14. Functional element 14 in this case may be introduced completely or partially into the slip. As shown in FIG. 2, functional element 14 may also be introduced repeatedly into the slip. In this case, three slip layers 20 are applied to functional layer 14, as shown in FIG. 2. Three slip layers 20 shown in FIG. 2 may in this case be made from the same slip or from different slips. For example, the slips may differ in terms of the amount of pore forming agent and layer thickness. Thus, the slips may be used, for example, in order to adjust the porosity gradient in a slip layer 20 formed from multiple slip layers. Thus, for example, the porosity may increase from a side 20 of slip layer 22 facing functional element 14 to a side 24 of slip layer 20 facing away from functional element 14.

The slip may, for example, be a highly fluid immersion slip capable of forming drops, in particular based on an organic solvent or water-based. The slip may, in particular, be filled with oxidic solids such as, for example, aluminum oxide, zirconium oxide, titanium oxide, pore forming agents such as, for example, vitreous carbon or wax, fine particle precious metal powder or precious metal salt such as, for example, platinum powder, palladium powder, rhodium powder or, for example, chlorides or nitrates thereof, fractions of binders and organic additives such as, for example, wetting agents, dispersants, defoaming agents for adjusting the rheological properties, solvents or water.

Functional element 14 may include at least one ceramic solid electrolyte 16 and at least one functional layer 18. For example, functional element 14 is present in the unsintered state or as already sintered functional element 14. For this reason, unsintered solid electrolyte 16 and slip layer 20 applied thereto may be sintered together. If functional element 14 is immersed repeatedly, an intermittent drying may take place between the individual immersing operations. In such case, drying may take place, for example, for a period of less than one hour at temperatures below 250° C. Sintering may take place at temperatures between 1200° C. and 1450° C.

Subsequently, slip layer 20 is then ground, at least in the area of the at least one functional layer 18. Grinding may take place with the aid of a corundum grinding belt or a grinding disk. This offers the advantage that sensor elements 10 may also be ground multiple times.

Figure 3:
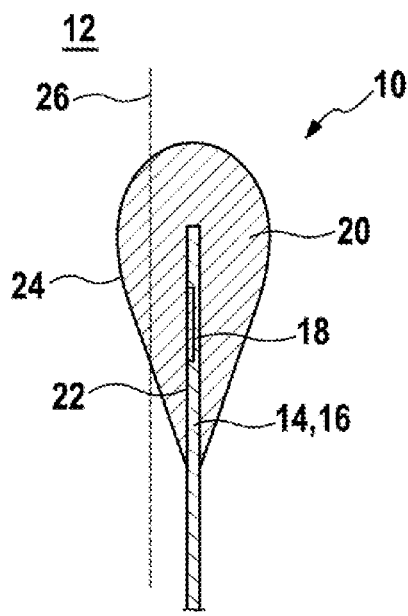
FIG. 3 shows a view of a cross section parallel to the direction of the layer structure and parallel to a longitudinal extension direction of the sensor element according to the present invention having a marking for a grinding site.

FIG. 3 shows a marking 26 at which grinding may take place. In particular, marking 26 indicates a grinding plane. Once ground, slip layer 20 exhibits a resulting layer thickness of 50 µm to 600 µm and preferably of 200 µm to 300 µm, for example, 250 µm. For example, slip layer 20 may be ground on one side above an outer electrode as functional layer 18 of a lambda sensor, or above a gas entry hole of a planar broadband lambda sensor. Above in this case indicates a layer level, which is situated above functional layer 18 in a direction as seen from functional element 14 to measuring gas space 12 perpendicular to the layer structure of sensor element 10.

This is followed by an impregnation process with, for example, a precious metal-containing preparation and/or a getter-containing solution. For example, an impregnating fluid may be applied to slip layer 20 at least in the area of the ground site with the aid of a drip process. For example, the impregnating fluid is applied in the form of a targeted, local wetting only above functional layer 18 due to a savings of precious metal, for example, with a platinum-containing and rhodium-containing impregnating fluid. Alternatively, however, an immersion method may be used in which functional element 14 and ground slip layer 20 are immersed into the impregnating fluid. The surface of slip layer 20 produced by grinding has a higher absorption capacity for the impregnating fluid than the adjacent non-ground areas. Accordingly, more impregnating fluid penetrates the ground areas of slip layer 20 than the non-ground areas.

This is followed by a thermal treatment of impregnated slip layer 20 such as, for example, a single baking, in order to fix the impregnation in slip layer 20. The method is concluded by carrying out a function test on sensor element 10.

Figure 4:
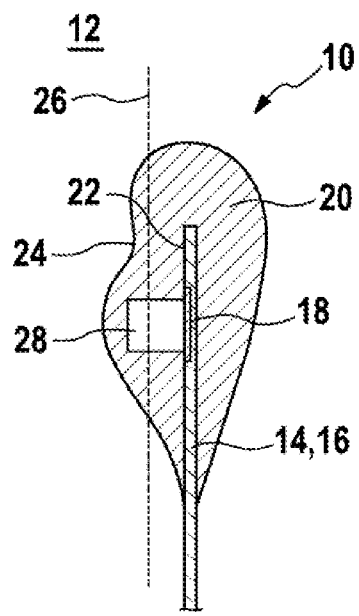
FIG. 4 shows a view of a cross section parallel to the direction of the layer structure and parallel to a longitudinal extension direction of a modified sensor element according to the present invention.

FIG. 4 shows a view of a cross section parallel to the direction of the layer structure and parallel to a longitudinal extension direction of a modified sensor element 10 according to the present invention. Hereinafter, only the differences relative to the aforementioned sensor element 10 are described. Sensor element 10 of FIG. 4 may be part of a planar broadband lambda sensor and includes a cavity 28 above a functional layer 18, which is delimited by slip layer 20. Functional layer 18 may, for example, be a gas entry hole. Cavity 28 may be produced by applying a cavity forming layer to an unsintered functional element 14 or an already sintered functional element 14, for example, using a cavity paste applied with the aid of a screen printing process. The cavity forming layer may, for example, include a highly filled vitreous glass paste. This is followed by applying slip layer 20 in the same manner as described above. During sintering, the cavity forming layer combusts, preferably residue-free, and leaves behind cavity 28. Slip layer 20 is ground at marking 26. The course of marking 26 in this case shows that by grinding slip layer 20, cavity 28 is exposed on one side facing measuring gas space 12, so that the measuring gas has free access to the gas entry hole. It is possible, however, for grinding to be carried out in such a way that cavity 28 remains separated from measuring gas space 12 by a thin slip layer 20, so that the measuring gas is able to pass through the pores in slip layer 20 to the gas entry hole. Following this are the above-described method steps of applying the impregnation, the thermal treatment of impregnated slip layer 20 and the function test of sensor element 10.

The manufacture according to the present invention of sensor element 10 is clearly apparent by viewing sensor element 10 and with supporting material analysis of sintered slip layer 20.

What is claimed is:

1. A method for manufacturing a sensor element for detecting a gas component in a measuring gas or a temperature of the measuring gas, comprising:

introducing at least one functional element at least once into at least one slip in such a way that a slip layer is applied to the functional element, the functional element including at least one solid electrolyte and at least one functional layer;

sintering the slip layer on the functional element;

grinding the sintered slip layer at least in the area of the at least one functional layer;

after the grinding, impregnating the ground slip layer using (i) a precious metal-containing solution or (ii) a getter-containing solution; and thermally treating the impregnated slip layer;

wherein the grinding includes grinding only a portion of the slip layer, wherein the ground portion of the slip layer has a higher absorption capacity for the impregnating precious metal-containing solution or getter-containing solution than adjacent non-ground areas of the slip layer, and wherein the impregnating step includes impregnating more of the precious metal-containing solution or getter-containing solution into the ground portion of the slip layer than into the adjacent non-ground areas of the slip layer.

2. The method as recited in claim 1, wherein the functional element is introduced repeatedly into the slip.

3. The method as recited in claim 2, further comprising: at least one drying process between the repeated introductions of the functional element into the slip.

4. The method as recited in claim 1, wherein a cavity forming layer is applied to the functional element prior to introduction into the slip.

5. The method as recited in claim 4, wherein the at least one slip layer, after sintering and grinding, has a thickness between 150 μm and 350 μm.

6. The method as recited in claim 4, wherein the functional element is introduced into the slip in a sintered state, and the slip layer is sintered on the functional element.

7. The method as recited in claim 1, wherein the functional element is introduced into the slip in an unsintered state, and the functional element and the slip layer are sintered together.

8. The method as recited in claim 1, wherein the grinding includes grinding the sintered slip layer at least in the area of the at least one functional layer using a corundum grinding belt or a grinding disk.

* * * * *